(12) United States Patent
Vartanian

(10) Patent No.: US 12,109,347 B2
(45) Date of Patent: Oct. 8, 2024

(54) DEVICE AND METHOD FOR ATRAUMATIC AND PERCUTANEOUS FORMATION OF AN ARTERIOVENOUS FISTULA

(71) Applicant: The Regents of the University of California, Oakland, CA (US)

(72) Inventor: Shant Vartanian, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/880,574

(22) Filed: Aug. 3, 2022

(65) Prior Publication Data

US 2022/0370700 A1    Nov. 24, 2022

Related U.S. Application Data

(63) Continuation of application No. 16/624,275, filed as application No. PCT/US2018/038236 on Jun. 19, 2018, now abandoned.
(Continued)

(51) Int. Cl.
  *A61B 17/11* (2006.01)
  *A61B 17/00* (2006.01)
  (Continued)

(52) U.S. Cl.
  CPC .......... *A61M 1/3655* (2013.01); *A61B 17/11* (2013.01); *A61M 1/3661* (2014.02);
  (Continued)

(58) Field of Classification Search
  CPC .... A61M 1/3655; A61M 1/3661; A61M 1/36; A61M 2039/0223; A61M 27/002;
  (Continued)

(56) References Cited

U.S. PATENT DOCUMENTS 5,895,404 A * 4/1999 Ruiz ...................... A61B 17/11
                                                        600/11
7,691,140 B2    4/2010 Bates et al.
(Continued)

FOREIGN PATENT DOCUMENTS

EP          1830905 B1    8/2016
WO      2013-192208 A    12/2013
WO   WO-2017124059 A1 *  7/2017    ........ A61M 25/0021

OTHER PUBLICATIONS

De Novo Classification Request for EVERLINQ® ENDOAVF System, De Novo Summary (DEN160006), 2016, 45 pages.
(Continued)

*Primary Examiner* — Philip R Wiest
*Assistant Examiner* — Linnae E. Raymond
(74) *Attorney, Agent, or Firm* — Brian E. Davy; Bozicevic, Field & Francis LLP

(57) ABSTRACT

Provided herein are novel devices for the formation of arteriovenous fistulas, which may aid subjects in need of hemodialysis. The novel devices are provided in a non-surgical procedure, greatly decreasing the cost and increasing the convenience of placing an arteriovenous fistula. The devices are atraumatic, and consist of a sutureless anastomosis device and conduit. Methods and tools for placing the devices in vivo are disclosed, including a magnetic-assisted method.

15 Claims, 13 Drawing Sheets

Related U.S. Application Data

(60) Provisional application No. 62/521,920, filed on Jun. 19, 2017.

(51) Int. Cl.
*A61B 90/00* (2016.01)
*A61M 1/36* (2006.01)
*A61M 39/02* (2006.01)

(52) U.S. Cl.
CPC ............... *A61M 39/0208* (2013.01); *A61B 2017/00862* (2013.01); *A61B 2017/00867* (2013.01); *A61B 2017/00876* (2013.01); *A61B 2017/1107* (2013.01); *A61B 2017/1139* (2013.01); *A61B 2090/3966* (2016.02); *A61M 2039/0223* (2013.01)

(58) Field of Classification Search
CPC .......... A61M 25/0194; A61M 25/0662; A61M 25/09041; A61M 25/0127; A61M 39/0208; A61B 17/11; A61B 17/083; A61B 2017/1107; A61B 2017/1139; A61B 2017/1135; A61B 2017/00243; A61B 2017/00252; A61B 2017/00876; A61B 2090/3966; A61F 2/06; A61F 2/064; A61F 2/07; A61F 2/90; A61F 2/91; A61F 2/88; A61F 2230/005; A61F 2230/0054
See application file for complete search history.

(56) References Cited

U.S. PATENT DOCUMENTS

| | | | |
|---|---|---|---|
| 7,846,172 B2 | 12/2010 | Makower | |
| 8,382,697 B2 * | 2/2013 | Brenneman | A61B 17/11 604/9 |
| 9,545,263 B2 * | 1/2017 | Lenihan | A61B 17/3403 |
| 9,724,170 B2 * | 8/2017 | Mickelsen | A61M 25/0606 |
| 10,603,040 B1 * | 3/2020 | Berman | A61B 18/1492 |
| 2005/0049675 A1 | 3/2005 | Wallace | |
| 2007/0173878 A1 * | 7/2007 | Heuser | A61B 17/3478 606/185 |
| 2008/0119879 A1 * | 5/2008 | Brenneman | A61B 17/3468 606/153 |
| 2009/0036872 A1 * | 2/2009 | Fitzgerald | A61M 25/0082 604/533 |
| 2010/0268316 A1 * | 10/2010 | Brenneman | A61B 17/11 623/1.11 |
| 2011/0054492 A1 | 3/2011 | Clark | |
| 2012/0065652 A1 * | 3/2012 | Cully | A61F 2/07 606/153 |
| 2012/0089089 A1 | 4/2012 | Swain et al. | |
| 2015/0148825 A1 | 5/2015 | Orion et al. | |
| 2015/0182358 A1 | 7/2015 | Florescu | |
| 2017/0087294 A1 | 3/2017 | Hull et al. | |
| 2018/0133441 A1 * | 5/2018 | Kellerman | A61M 25/0127 |
| 2020/0289796 A1 * | 9/2020 | Kurth | A61B 17/0057 |
| 2022/0370700 A1 | 11/2022 | Vartanian | |

OTHER PUBLICATIONS

Erdmann et al. (2004) "Side-to-side sutureless vascular anastomosis with magnets" Journal of Vascular Surgery, 40(3):505-511.

Klima et al. (2003) "Magnetic vascular coupling for distal anastomosis in coronary artery bypass grafting: A multicenter trial" Evolving Technology, 1568-1574.

Klima et al. (2004) "Magnetic Vascular Port in Minimally Invasive Direct Coronary Artery Bypass Grafting" Circulation, II-55-II-60.

Lee et al. (2023) "The Evolving Use of Magnets in Surgery: Biomedical Considerations and a Review of Their Current Applications" Bioengineering, 10, 442, 16 pages.

* cited by examiner

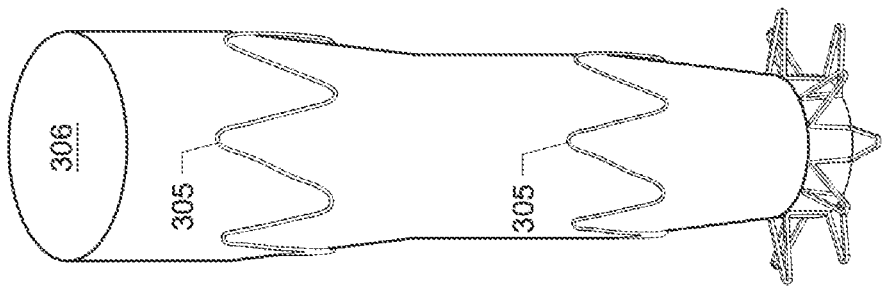
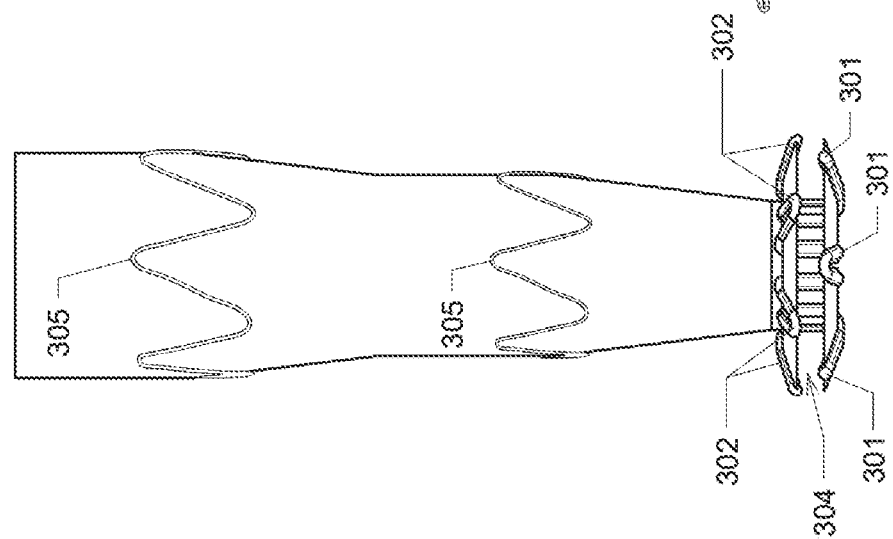
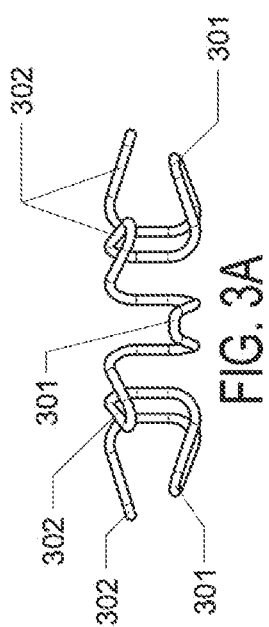
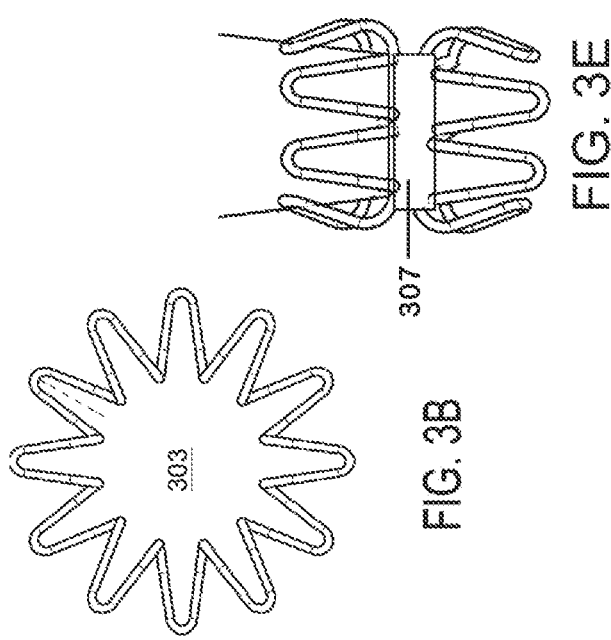

DEVICE AND METHOD FOR ATRAUMATIC AND PERCUTANEOUS FORMATION OF AN ARTERIOVENOUS FISTULA

CROSS-REFERENCE TO RELATED APPLICATIONS

This application is a continuation application of U.S. patent application Ser. No. 16/624,275, entitled "Device and Method for Atraumatic and Percutaneous Formation of an Arteriovenous Fistula," filed on Dec. 18, 2019, which is a 35USC § 371 national stage filing of International Application number PCT/US2018/038236, entitled "Device and Method for Atraumatic and Percutaneous Formation of an Arteriovenous Fistula," filed on Jun. 19, 2018, which claims priority to U.S. Provisional Application No. 62/521,920, entitled "Device and Method for Atraumatic and Percutaneous Formation of an Arteriovenous Fistula," filed on Jun. 19, 2017, each of which applications is incorporated by reference herein in its entirety.

STATEMENT REGARDING FEDERALLY SPONSORED RESEARCH OR DEVELOPMENT

Not applicable.

BACKGROUND OF THE INVENTION

Millions of people worldwide suffer from end-stage renal disease or other conditions requiring hemodialysis treatment. Hemodialysis requires accessing the circulatory system for the withdrawal, cleansing, and return of the patient's blood. Methods of accessing the patient's circulatory system include tunneled catheters, arteriovenous grafts, and arteriovenous fistulas (AVFs). The type of circulatory access used in hemodialysis has important consequences for the patient. Of these methods, it is widely accepted that AVFs have the best outcomes, with the lowest risk of morbidity and mortality for the patient. AVFs are less prone to infection and are more durable than both tunneled catheters and arteriovenous grafts. However, the current method of placing an AVF is a surgical procedure, requiring the services of highly trained personnel (e.g. surgeons, anesthesiologists, etc.) and the use of associated operating room equipment. Such resources are expensive and in short supply in some communities, creating practical, economic, and medical barriers to AVF placement. As a result, less than 30% of patients in the United States initiate hemodialysis with AVFs, with the majority using inferior tunneled catheter access.

Accordingly, there is a need in the art for devices and procedures that simplify AVF formation. Various methods of creating percutaneous AVF's have been developed. A first set of AVF technologies includes device-based methods of forming AVFs, encompassing various implants and surgical methods. Exemplary systems are described in: PCT International Patent Application Publication Number WO201392208, entitled "Stent to Assist in Arteriovenous Fistula Formation," by Florescu; United States Patent Application Publication Number 20110054492, entitled "Medical Device for Repairing a Fistula," by Clark; and U.S. Pat. No. 7,691,140, entitled "Anastomosis device for vascular access," by Bates et al. The majority of these mechanical AVF solutions employ barbs, hooks, and other features that increase trauma to the treated area, and none of these prior art methods or devices have been widely adopted.

A second type of AVF technology is tissue welding, encompassing fusion of tissues using thermal, electrical, RF, or laser energy. Exemplary tissue welding systems include the EVERLINQ™ system (TVA Medical Systems, Austin, Texas, USA); systems described in U.S. Pat. No. 9,017,323, entitled "Devices and Methods of Forming a Fistula," by Miller et al.; and the ELLIPSYS™ system (Avenu Medical, San Juan Capistrano, California, USA). However, tissue welding technologies have risks associated with off-target thermal injury, resulting in nerve injury, pain, necrosis and other complications. Furthermore, some tissue welding systems create a fistula without providing any means to direct blood flow into the superficial venous system, resulting in the need for a second endovascular or surgical procedure to create a functional AVF.

Accordingly, there remains a need in the art for novel AVF methodologies that are clinically practical, cost effective, and which avoid the side effects and potential need for additional interventions associated with tissue welding.

SUMMARY OF THE INVENTION

Provided herein are novel devices and methods for the percutaneous formation of AVFs. The novel inventions disclosed herein enable the efficient and economical placement of fistulas such as AVFs. The systems described herein encompass novel devices, novel methods, and various improvements to the art. In one aspect, the scope of the invention encompasses the novel deployment of atraumatic anastomosis devices in the context of fistula formation. In one aspect, the scope of the invention encompasses the novel use of a fistula implant comprising a conduit for creating optimized blood flows at the fistula site. In one aspect, the scope of the invention encompasses novel nonsurgical methods of forming fistulas. In one aspect, the scope of the invention encompasses novel placement methods that enable inexpensive and facile fistula creation.

The methods of the invention advantageously allow the placement of the implant and formation of an AVF in a minimally invasive, atraumatic, endovascular procedure. This allows placement in a clinical venue, rather than surgical setting, without need for subspecialty care such as anesthesia or surgical staff. This greatly reduces the practical and economic barriers to the installation of an AVF, as compared to current surgical methods required for AVF installation.

BRIEF DESCRIPTION OF THE DRAWINGS

FIG. 1A depicts the vascular system of the arm. Site 102 is a potential target area for formation of an AVF between the venous perforator branch in the antecubital fossa and the distal brachial artery 103, or between the venous perforator branch in the antecubital fossa and either the proximal radial or proximal ulnar artery, just beyond the brachial artery bifurcation. Site 101 is a potential introduction site for introducing the crossing device. Potential introduction sites for introducing the complementary placement device are in the radial artery 105 or ulnar artery 104. FIGS. 1B and 1C depict surgical AVF sites and connections.

FIGS. 2A, 2B, 2C, 2D, 2E, 2F, 2G, 2H, and 2I depict an exemplary implementation of the invention wherein the implant of the invention is deployed to connect a first and a second blood vessel by use of a crossing device and complementary placement device. 2A: The crossing device 201 is advanced through the first blood vessel 203 to the target site. Next, the complementary placement device 215 is advanced through the second vessel 205 to the target site. 2B: the magnetized tip 202 of the crossing device 201 attracts the magnetized tip 208 of the complementary placement device 215 with sufficient force to pull the wall 204 of the first vessel into proximity with the wall 206 of the second vessel. 2C: Cutting element 209 is deployed from the tip 202 of the crossing device, piercing the first and second vessel walls (204 and 206) and entering a hollow interior portion 207 of the complementary placement device 215. The cutting element may be retracted or remain in the hollow interior of the placement device. 2D: A guide wire 210 is extended from the tip 202 of the crossing device 201 and extended into the hollow cavity channel 207 of the placement device in the second vessel 205. 2E: The tip 202 of the crossing device 201 is extended into the second vessel 205 by the opening created by the cutting tool. 2F: The implant is partially ejected such that the first set of hands 211 is deployed from the tip 202 of the crossing device, inside vessel 205. 2G: The crossing device is withdrawn such that the tip 202 is pulled back into the first vessel 203. The first set of hands catches and pulls the wall 206 of the second vessel snugly against the wall 204 of the first vessel. 2H: The implant is further ejected from the tip 202 of the crossing device 201 such that the second set of hands 212 of the implant is ejected from and are deployed such that the wall 204 of the first vessel and the wall 206 of the second vessel are sandwiched between the first set of hands 211 and the second set of hands 212. 2I: The crossing device 201 is withdrawn, releasing the conduit 213 of the implant from the crossing device and leaving it in place in the first vessel 203, with a fistula created between vessels 203 and 205 created by the central annular section of the implant (not visible in this view).

FIGS. 3A, 3B, 3C, 3D and 3E. FIGS. 3A, 3B, 3C, 3D, and 3E depict various elements of the implant of the invention. FIG. 3A depicts a section of an exemplary sutureless anastomosis device comprising a piece of nitinol wire bent to create a bottom row of hands 301 and a top row of hands 302. As depicted here in the relaxed configuration, the hands are substantially perpendicular to the longitudinal axis of the implant and the row of hands 301 and 302 form two parallel flanges. FIG. 3B depicts a top view of the sutureless anastomosis device comprising a hollow central portion 303. FIG. 3C depicts a side view of the entire implant, including the bottom hands 301 and top hands 302, connected to conduit 305. The conduit comprises a scaffolding 305. FIG. 3D is a perspective view of the implant, making visible the hollow inner lumen portion 306 of the conduit. FIG. 3E depicts the hands in the deflected, tensioned position as they would be when stored in the implant housing of the crossing device, with the hands deflected from their resting position around the annular structure 307.

FIGS. 4A, 4B, 4C, 4D, and 4E depict an exemplary process for placing the implant by use of a crossing device without the aid of a complementary placement device to create an AVF between the venous perforator branch and brachial artery. FIG. 4A depicts a cutting element 402 and guide wire 403 extended from the distal tip 404 of the crossing device 401 across the vein wall into the adjacent artery. FIG. 4B depicts a first set of hands 405 deployed from the tip of the crossing device. FIG. 4C depicts the tip of the implant being withdrawn back into the vein with the hands 405 pulling the artery wall. FIG. 4D depicts the second set of hands 406 of the distal portion of the implant (inset) being deployed to sandwich the vein and artery walls together. FIG. 4E depicts the crossing device having been withdrawn, deploying the second set of hands 409 and the conduit portion 408 of the implant in the vein. Blood flowing through the fistula is directed to the peripheral venous system 410, bypassing the deep venous system region 411 at which the fistula is formed.

DETAILED DESCRIPTION OF THE INVENTION

Figure 1A:
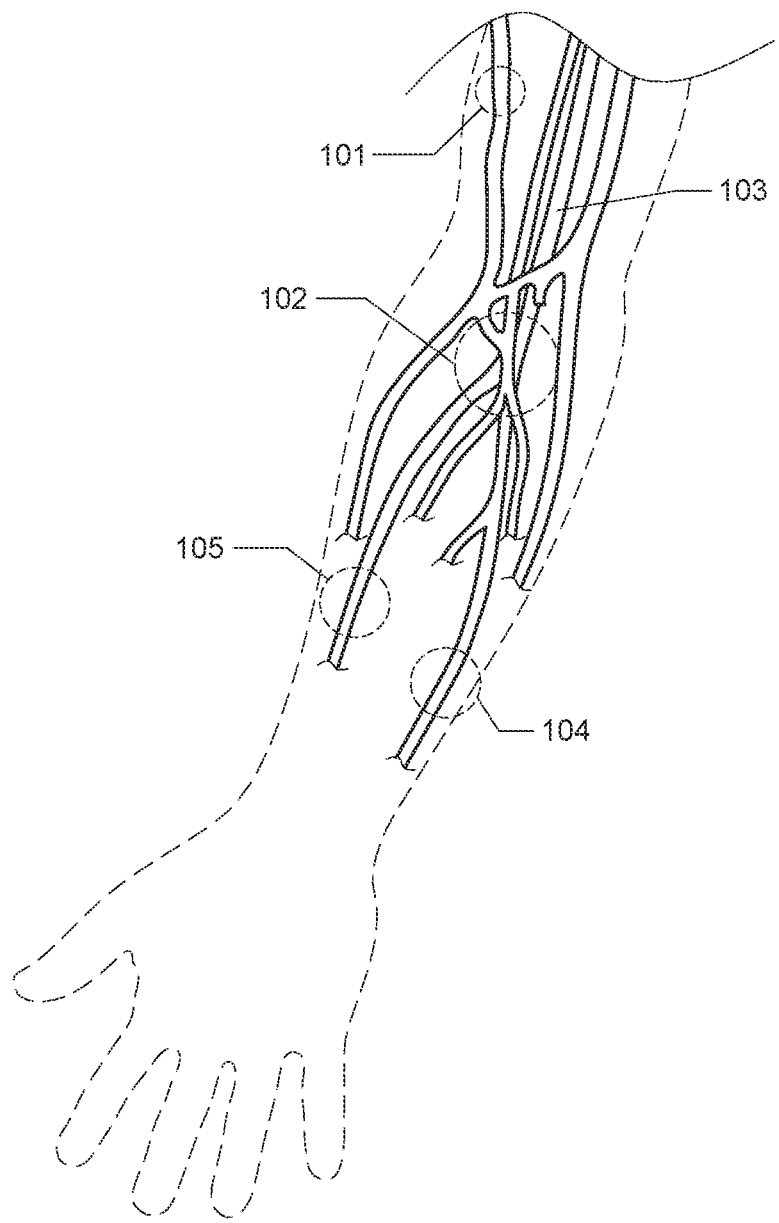
FIGS. 1A, 1B, and 1C.
Figure 1B:
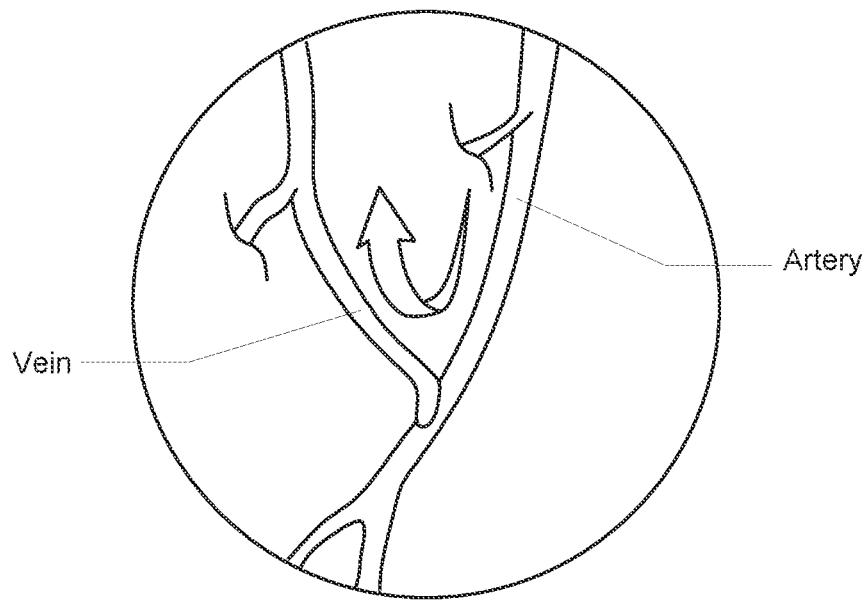
Figure 1C:
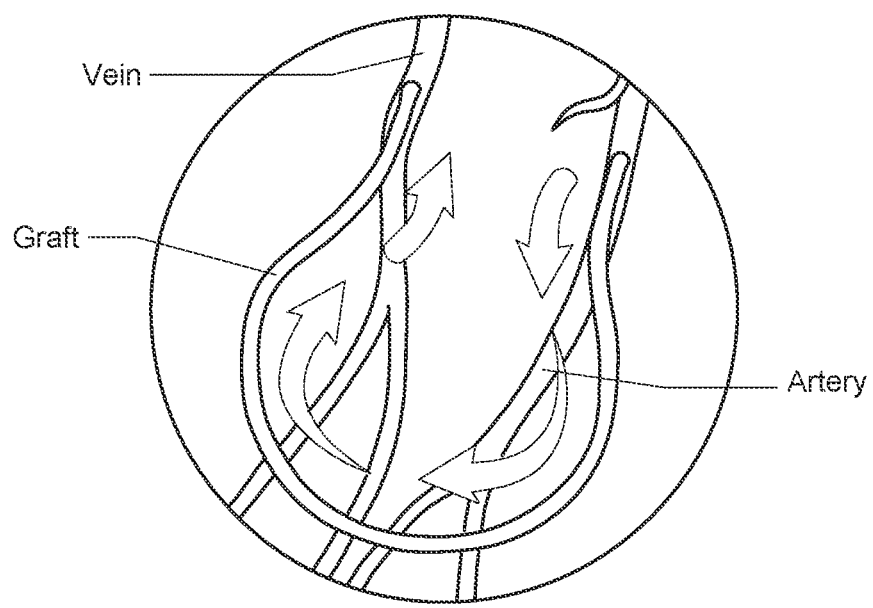

Various elements of the invention are described herein as having a "proximal" and a "distal" end. "Distal" and "proximal," as used herein, are defined with respect to the operator (i.e., the medical person or persons that are implanting the device in the patient). Accordingly, the proximal end is that end that is closest to the operator and the opposite, distal end is that end which is inserted first and furthest into the patient.

Various parameters are described herein as being "within the range" of two numbers. Such reference will encompass the stated values and all values intermediate thereto. For example, if a parameter is stated to be in the range of 2-3 units, this will encompass all values greater than or equal to two and less than or equal to three.

The various elements of the invention are described next.

Arteriovenous Fistula. The various inventions disclosed herein are directed to methods of forming a fistula, i.e., a connection between any two blood vessels that enables blood flow between them. The inventions are especially well suited to the formation of arteriovenous fistulas (AVFs), i.e. a connection between an artery and a vein.

The AVFs of the invention may be formed in any part of the body. In a preferred implementation, the AVFs of the invention are formed in the upper arm at a point where the venous perforator branch in the antecubital fossa, which connects the superficial venous system to the brachial veins, is in close proximity to the distal brachial artery or proximal radial or ulnar artery, just beyond the brachial artery bifurcation. The proximity of these blood vessels to each other creates an anatomic opportunity for minimally invasive creation of AVFs. Accordingly, the description provided herein will be made with reference to creation of AVFs at this site. However, it will be understood by one of skill in the art that the devices and method of the invention may be applied and adapted to other regions of the body, including the lower extremities, wherein it is practical to connect veins and arteries.

AVF Implant. In one aspect, the scope of the invention encompasses a novel implantable device for creating an AVF. An exemplary embodiment of the device is illustrated in FIGS. 3C and 3D. The implantable device will be referred to herein as the "implant". The distal end of the device is that end of the tubular body which forms the anastomosis between the vein and artery. Proximal to this anastomosis-forming component and connected thereto, the implant comprises a conduit component. In an AVF type fistula, the conduit is placed the venous blood vessel of the fistula and directs the outflow of blood from the arterial vessel into the vein. The novel conduit component confers several advantages. The conduit acts as a bypass to direct outflow of blood from the arterial vessel away from the site of the fistula. When the AVF is formed in a location that has a perforator branch connecting the superficial venous system to the venous system, for example, wherein the first blood vessel is the median cubital perforator, connecting to either the medial cubital vein, cephalic vein or basilic vein of the arm and the second blood vessel is the brachial artery at its terminus (or the proximal radial or proximal ulnar arteries), the conduit can be placed such that it directs blood flow away from the deep system to the superficial system, creating a favorable state of flow. This avoids the need for secondary interventions such as embolization, speeds maturation of the target vein and results in quicker time to first cannulation.

The conduit component is a substantially tubular body having an outer diameter, at its widest point, of about 100-150% of the diameter of lumen of the vein in which it will be placed, with dimensions that ensure snug fit against the vessel wall. Exemplary diameters of the conduit component are in the range of 2-9 mm, for example, in the range of 2-3 mm, in the range of 3-4 mm, in the range of 4-5 mm, in the range of 5-6 mm, in the range of 7-8 mm, in the range of 8-9 mm. The tubular body may be tapered at its distal end, for example as depicted in FIG. 3D, with a diameter, for example, in the range of 1-6 mm at its narrow, distal end, for example, in the range of 1-2 mm, in the range of 2-3 mm, in the range of 3-4 mm, in the range of 4-5 mm, in the range of 5-6 mm, or in excess of 6 mm. The taper provides for a smoother blood flow path into the vein, for example, the antecubital vein, and avoids turbulent blood flow that can cause complications such as clotting. The length of the conduit body may be in the range of 5-35 mm. In various implementations, the length of the conduit is in the range of 5-8 mm, in the range of 8-10 mm, in the range of 10-12 mm, in the range of 12-15 mm, in the range of 15-18 mm, in the range of 18-20 mm, or in excess of 20 mm. In a preferred implementation, the length of the conduit is at least 15 mm to ensure that blood flowing from the artery into the cubital vein will bypass the deep venous system, increasing flow into the superficial cephalic vein.

The composition and configuration of the conduit component may vary. In one embodiment, the conduit component comprises a metal scaffolding, covered by or embedded within a fabric or film of biocompatible material. The metal scaffolding may comprise any metal lattice design, such as that found in stents, as known in the art. For example, the scaffolding may comprise a wire frame made up of interconnected, substantially parallel rows of interwoven metallic wires or like elements, for example, in an undulating "zig-zag" or wave pattern, forming a lattice or cage-like structure. In one embodiment, the peaks of the zig-zag pattern are aligned in the longitudinal axis. In another embodiment, the lattice is a mesh, for example, a mesh comprising two sets of multiple, parallel rows of wire meeting at a right angle (creating square spaces between wires) or off-axis (creating trapezoidal spaces between wires). In another embodiment, the scaffolding may comprise one or more spiral elements (e.g., parallel or crossing elements) which encircle the conduit from its distal to its proximal ends.

The thickness of the wire may be any thickness that creates the desired rigidity of the conduit portion. For example, wires of thickness of 0.1 to 0.2 mm microns may be used.

The metal may comprise stainless steel, nitinol, cobalt chromium or other biocompatible metals known in the art, or a combination of the above. In an alternative embodiment, the scaffolding comprises an elastic polymeric material rather than metal.

The scaffolding of the conduit may be manufactured by a suitable means known in the art. For example, in the case of metal scaffolding, the structure may be manufactured by laser cutting of a metal tube using a finely controlled and focused laser beam and rotation of the working surface, as known in the art. Metal thickness in the range of 0.1-0.2 mm may be used.

The covering may comprise polytetrafluoroethylene (PTFE), or other materials, such as synthetic polyester terephthalate textile for example, materials used in covered stents. The covering may comprise fibrous materials in a woven or braided fabric, or may comprise a film. The covering may be porous. This use of PTFE or other prosthetic material covering the metal scaffolding aids in preventing pseudoaneurysm formation during percutaneous access creation.

The covering may cover the scaffolding, for example being wrapped or spooled around the scaffolding. For example, in one embodiment, the scaffolding is encapsulated between two sheets of covering material, such as PTFE. Alternatively, the scaffolding may be integral to the covering, being made by dipping, spraying, or otherwise coating the scaffolding with the covering material. In one embodiment scaffolding is placed over a form which defines the tapered inner lumen of the conduit, over which the scaffolding is placed prior to dipping, coating, or otherwise applying the covering.

The conduit will preferably be partially rigid, being rigid enough in the radial axis to hold the shape of the lumen and maintain blood flow, with some degree of give to avoid tissue injury. In the longitudinal axis, the conduit may be sufficiently flexible to bend with movement of the subject in which it is implanted. In one embodiment, the flexibility of the conduit is consistent across the length of the structure. In one embodiment, the rigidity of the conduit is variable across the length of the structure. Rigidity, in general or locally, may be tuned by the design of the scaffolding and/or covering material, for example, by varying the thickness of the wires, the spacing between rows of wires, the frequency and size of elements interconnecting the rows, the thickness of the covering layer, etc.

In one embodiment, the conduit is coated with one or more agents. For example, the conduit may be coated with antibiotics, blood thinners, anti-inflammatory compounds, anti-proliferative compounds, pro-maturation compounds or other agents that facilitate healing, durability or prevention of infection.

The distal end of the implant comprises a sutureless anastomosis device. The sutureless anastomosis device comprises any device that can form an anastomosis without the requirement for sutures. Generally, once deployed in situ, the sutureless anastomosis device will comprise a ring structure capped by two parallel flanges, wherein the arterial and venous walls of the AVF are sandwiched together between the flanges, wherein the central aperture of the ring creates a fluid connection between the adjoined artery and vein.

In an exemplary embodiment, as depicted in FIGS. 3C and 3D, the sutureless anastomosis device comprises the following basic elements: an annular body; a first set of deployable hands, a second set of deployable hands. The annular body comprises a ring, for example, a ring made of wire elements, for example as depicted in FIGS. 3A and 3B. In the transverse dimension, the annular body defines a central hole or opening having a diameter, as in 303 of FIG. 3B. The inner diameter of the annular body defines the opening of the AVF when placed in situ. The inner diameter of the annular body may be in the range of 1-5 mm, for example, in the range of 1-2 mm, in the range of 2-3 mm, in the range of 3-4 mm, in the range of 4-5 mm, or in the range of 5-6 mm. For example, in one embodiment, the diameter of the opening is in the range of 3.0-4.0 mm, for example, 3.5 mm. In the longitudinal or axial direction, the annular body comprises a cylindrical body having a height, the height being defined by the spacing between the upper and lower flanges created when the device is deployed, for example as denoted 304 in FIG. 3D. The height should be about equal to the combined thickness of the blood vessel walls which will be joined to form the fistula, for example, the artery wall and the vein wall in an AVF. For example, the height may be in the range of 0.25-1.0 mm, for example, in the range of 0.25 to 0.5 mm, in the range of 0.5 to 0.7 mm, or in the range of 0.5 to 1.0 mm.

The sutureless anastomosis device comprises two sets of what will be termed "deployable hands." These structures are termed "hands" to emphasize their function of clasping the vessel walls together without puncturing the walls. Each set of deployable hands comprises two or more substantially flat or gently curved projections which extend radially from the annular body, when in the deployed configuration. The deployable hands may comprise loops, for example, substantially U-shaped loops, V-shaped loops, or semi-circular loops. Each set of deployable hands may comprise any number, for example, from two to sixteen hands, for example, two, three, four, five, six, seven, eight, nine, or ten or twelve hands. With the aid of a crossing device, described below, each set of hands can be delivered to the site of the AVF in a first, stowed position, i.e. in a configuration wherein the hands are oriented substantially parallel to the axial axis of the implant. The hands can be deployed, for example, by releasing them from the constraints of the deployment instrument, such that they assume a relaxed position extending radially from the annular body (FIG. 3D). In one implementation, the hands, in the deployed position, extend substantially at 90 degrees from the body, i.e. perpendicular to the annular body. In other implementations, the hands may project at an angle varying from 45 to 135 degrees from the longitudinal axis of the implant.

The hands may comprise an elastic or superelastic malleable metal with shape memory, such as nitinol, which can be cut to create hands that radially project from the annular body (i.e. the "relaxed" or "deployed position"). Under tension, the hands can be deflected from their relaxed, horizontal position to assume a vertical (i.e., parallel to the longitudinal axis of the implant) stowed, tensioned configuration, for example when contained under pressure within a deployment device. Upon being released from the constraints of the deployment device, the resilient memory metal comprising each hand flips or folds back to its relaxed position, such that the hands in each row are projecting radially from the annular body, collectively forming a flange. The length of the hands may be, for example, in the range of 0.5-2.0 mm, for example, in the range of 0.25 to 0.5 mm, in the range of 0.5 to 0.75 mm, in the range of 0.75 to 1 mm, in the range of 1.0 to 1.25 mm, in the range of 1.25 to 1.5 mm, in the range of 1.5 to 1.75 mm, or in the range of 1.75 to 2.0 mm.

The first set of deployable hands is located at the distal end of the annular body (FIG. 3D). The first set of hands may be deployed independently of the second set of hands. The second set of deployable hands is located at the proximal end of the annular body. The second set of hands may be deployed independently of the first set of hands.

The sutureless anastomosis device will be attached or integrated with the conduit portion of the implant. The sutureless anastomosis device will encircle the distal end of the lumen of the tubular conduit, such that fluid flow through the central aperture of the annular element will proceed into the conduit. In another embodiment, the sutureless anastomosis device and the scaffolding of the conduit are formed from a single piece of material, e.g. a metal tube, for example, a metal tube laser cut to create the wire elements of the scaffolding and sutureless anastomosis device. In one embodiment, the sutureless anastomosis device is manufactured separately from the conduit and is joined thereto by one or more connecters that attach it to the conduit portion of the implant. The connectors may comprise hooks, barbs, fabric, textile or loops that connect to the scaffolding portion of the conduit element, which pierce or extend into the conduit material, or which otherwise hold the sutureless anastomosis device and conduit together.

The sutureless anastomosis device may comprise any sutureless anastomosis device known in the art. For example, the sutureless anastomosis element may comprise devices, or variants thereof, described in: U.S. Pat. No. 6,152,937, entitled "Medical Graft Connector and Method of Making and Installing Same," by Peterson; U.S. Pat. No. 5,916,226, entitled "Apparatus and method for improved sutureless anastomosis," by Tozzi; U.S. Pat. No. 6,440,143, entitled "Medical Anastomosis Apparatus," by Swanson et al.; United States Patent Application Publication Number 20050049675, entitled "Medical Devices and Related Methods," by Wallace; United States Patent Application Publication Number 2012/0123512, entitled "Sutureless Vascular Anastomosis Connection," by Asfora et al. In one embodiment, the sutureless anastomotic device comprises a device such as the Symmetry Bypass System Aortic Connector™ (St Jude Medical Inc, St. Paul MN).

In a preferred implementation, the sutureless anastomosis device does not comprise any barbs, hooks, or other structures that puncture the blood vessel walls. Accordingly, the device enables atraumatic creation of AVFs. In an alternative implementation, the sutureless anastomosis device comprises one or more barbs, hooks, or like structures that perforate the target blood vessels to aid in securing the device in place.

In situ, over time AVF lumens tend to become partially occluded by hyperplastic tissue, thrombus or other biological deposits. Accordingly, in some implementations, the annular structure of the anastomosis device is expandable. For example, the expandable annular structure may comprise a plurality of radially expandable wire segments arranged radially around the circumference of the annular element. The elements may comprise, for example, folded wires, struts, U-shaped wire elements, V-shaped wire dements, or elements otherwise configured to expand under radial pressure exerted within the central lumen to increase the diameter of the central lumen. The individually expandable elements, collectively may be forced to unfold, flatten, or otherwise deform such that the diameter of the lumen is maintained. Any number of such elements may be present, for example, 2, 4, 6, 8, 10, 12, or more expandable elements. This ability to expand allows the annular element to be expanded beyond the nominal deployment diameter in order to maintain a diameter effective for sufficient blood flow from the artery to the adjoined vein (e.g. 2-5 mm), for example by periodic stretching with a catheter (e.g. balloon catheter) or like instrument inserted into the AVF aperture. Using an expandable annular element, the AVF may be maintained at an effective diameter for longer periods of time than static AVFs, using a minimally invasive (e.g. percutaneous) ultrasound guided procedure to expand the ring.

Crossing Device. The implant of the invention may be placed in situ to create a fistula by the use of a crossing device. The crossing device may comprise a single device or combination of devices which allows for the positioning and placement of the implant to create the fistula, e.g., an AVF.

A first element of the crossing system is the implant housing. The implant housing is an assembly at the distal end of the crossing device. The implant housing comprises a device in which the implant can be stowed, delivered to the site of the fistula to be formed, and deployed to form the fistula. The housing is configured to position and release the implant in a controlled manner to create the fistula.

At the proximal end of the crossing device is an assembly called the control assembly. The control assembly comprises various control structures, which may be actuated to operate the elements of the distal implant housing assembly. The proximal control assembly is configured to be ex-vivo, outside the body and to be operated by one or more persons.

Connecting the proximal control assembly and the distal implant housing assembly is an intermediate section comprising a catheter, which houses the wires or other structures which control the elements distal implant housing.

The implant housing assembly is compact and generally cylindrical, configured for movement through a blood vessel to its target position. In general, the distal implant housing assembly will have a diameter in the range of 70-150% of the inner diameter of the blood vessel through which it will be deployed. For example, a diameter in the range of 70-90% of the diameter of the vessel is preferred for easy travel through the vessel, however, larger diameters may be used in which the vessel is distended by the housing. For placement in the cubital artery, for example, in an average-sized adult, the diameter of the housing will be in the range of 1.3-2.3 mm (4-7 french). The implant housing may be coated with a low friction polymer, such as silicone or PTFE, to ease the movement of the implant housing through tortuous vessels.

A first function of the implant housing is stowage of the implant and enabling its controlled release to form the fistula when positioned at the target site. In one embodiment, implant housing comprises an outer covering and an inner core. The implant is stowed in a compressed conformation, within the annular space between the outer housing and the inner core. In the compressed conformation, the first and second set of hands are deflected so as to be substantially parallel with the longitudinal axis of the crossing device. At the distal end of the outer housing, the annular space created between the inner core and outer housing is open, or may be selectively opened by the operator by the use of actuators controlled at the proximal end. This opening will be referred to herein as the "implant exit."

Continuous with the inner core, and extending beyond the distal end of the outer housing is the distal tip. The distal tip of the implant housing comprises a rounded or tapered tip which facilitates the movement of the implant housing through the blood vessels to the target site.

The distal tip of the crossing device will comprise one or more markings which aid in visualization of the distal implant housing assembly for its guided movement through the blood vessels and its placement at the target site. In one embodiment, the one or more markings comprise echogenic markings which are visible using imaging modalities such as ultrasound. Such markings may be made of thermoplastic material or metal (e.g., stainless steel) or may comprise of a surface that has been etched, dimpled or roughened in a manner to enhance detection by ultrasound equipment. In one embodiment, the markings comprise radio-opaque markings, comprising gold, platinum, or other radiopaque materials that can be readily imaged by a radiographic imaging modality, e.g. fluoroscopy. One or more markings may be present on the implant as well, or the implant may comprise a material that is capable of being imaged using an external imaging modality.

In one embodiment, the crossing device comprises one or more magnetic elements at the distal tip. The magnetic element may be used in those implementations of the system that employ complementary catheters for precise placement of the distal implant housing assembly at the target site, as described below.

In one implementation, the implant housing comprises one or more deployable cutting elements for piercing the walls of the vessels to be joined. For example, in one embodiment, the distal tip forms a housing in which a retractable cutting element is housed, which such cutting element can be advanced axially from the distal tip in order to pierce, cut, or otherwise create an aperture in the vein wall and to further create an aperture in the adjoining artery to which the vein will be connected. The cutting element may be extended and retracted by the means of an actuator, the actuator being in connection with a control element in the control assembly at the proximal end of the device. The cutting element may comprise a needle, blade, or other cutting instrument. In one embodiment, the cutting element is a needle wire, i.e. a wire with a needle tip.

The implant housing contains one or more actuators. The one or more actuators can be engaged, by controls at the proximal end of the device, to advance the implant in the distal direction. The actuators may comprise any structure or device which controllably advances the implant towards the implant exit. In one embodiment, the actuator is a piston connected to a cable that extends to a control element at the proximal end of the device, such that movement of the control element directly actuates the piston, which pushes on the implant in the distal direction. For example, in one embodiment, the piston comprises a ring that fits within the annular space between the outer housing and the core. In another embodiment, the actuator is a spring-loaded or otherwise tensioned actuator that can be released by means of a latch in connection with a cable that connects the latch to a control element at the proximal end, such that the operator can release the spring loaded actuator, which will advance the implant from the implant exit by a fixed distance. In another embodiment, the actuator is a motorized device that will advance the implant from the implant exit by a fixed distance (e.g. stepper motor) or by a distance controlled by the operator at the proximal end.

The various elements of the distal implant housing assembly, for example, the actuators that deploy the implant, or actuator that deploy the cutting element, if present, will be responsive to the control structures at the proximal control housing. The proximal control housing is configured to remain ex-vivo, outside the patient, where it is accessible to an operator. The control assembly will comprise controls, for example, knobs, screws, gears, ratchets, plungers, and other mechanical controls, or electronic control elements that can operate the actuators in the distal implant housing assembly.

The proximal control end of the crossing system is in mechanical and control connection with the distal implant housing assembly by a catheter, or like structure, that can be advanced through blood vessels. The catheter will comprise comprising cables, wires, hydraulic channels, moveable rods or other elements for the transmission of mechanical forces through endoscopic instruments. Alternatively, the control assembly comprises electronic control elements which are in electrical connection with powered actuators in the implant housing, such that signals transmitted through the catheter can be used to operate mechanical elements in the housing and which can house wires, cables, or other elements connecting the control structures at the proximal end with actuator elements at the distal end. For example, the catheter may comprise thermoplastic materials, resins, metal (e.g. stainless steel wire braid) or combinations thereof. The catheter length will be any sufficient to reach the target site from the selected entry point, for example, in the range of 20-30 cm.

The crossing device may further comprise a guide wire for aiding the movement of the distal implant housing assembly through the blood vessel to the target site. The guide wire may be housed in a channel of the intermediate catheter section, and may be extended from a port present in the distal implant housing assembly, controlled at the control assembly by means known in the art. Any vascular guide wire may be used, for example, metal core wires, polymeric wires, and other designs known in the art, for example, in typical sizes such as 0.46 mm, 0.64 mm, or 0.81 mm diameters In an alternative embodiment, the guide wire is a needle wire, i.e. a wire with a needle tip that is deployed to act as both the cutting element and the guide wire.

In one implementation, the crossing device is operated in combination with a second, complementary placement device. The complementary placement device comprises a catheter with a tip, for example, a rounded tip. The tip comprises one or more magnets. The tip may optionally comprise a hollow channel for receiving the guide wire of the crossing device, for example, a central channel with an opening at the distal end of the placement device, extending for a portion of the distal end of the placement device.

In this implementation, the implant housing assembly comprises one or more magnets at the distal tip. The complementary placement device comprises a catheter with a distal tip also comprising one or more magnets. The one or more magnets of the crossing device tip and the placement device tip may comprise neodymium magnets or other type of magnet known in the art. In one embodiment, the magnetic element is an electromagnet, powered by a power source in the control housing via wires in the catheter. The magnets of the crossing device tip and/or placement device tip may comprise a ring or doughnut shaped magnet that define or circumscribe the end face of the device, the center portion being hollow for the advancement of the implant through the end of the crossing device and for receiving the cutting element and guide wire in the case of the placement device. In the implementation of the invention utilizing magnet-assisted placement, the implant housing assembly of the crossing device is advanced to the target site in a first blood vessel and the placement device tip is advanced to the target site in a second blood vessel, wherein, when in sufficient proximity, the magnets will be of sufficient force to attract each other and push the walls of the two vessels together between the two magnetized tips. This enables precisely targeted deployment of the cutting element to pierce both vessels. In one embodiment, magnets are present on both the implant housing and the tip of the placement device. In another embodiment, one of the implant housing or tip of the placement device comprises a magnet while the other comprises one or more ferromagnetic metal elements that attracted to the magnet(s) on the complementary device.

The implant housing may be coated with a low friction polymer, such as silicone or PTFE, to ease the movement of the implant housing through tortuous vessels.

Methods of Use. The scope of the invention further encompasses methods of using the devices described herein to create fistulas, e.g., AVFs. In a general method, the scope of the invention encompasses a method as follows:

a method of forming a fistula comprising a connection between a first and a second blood vessel in a subject, comprising the following steps:
  an access is created at a selected entry site of the subject;
  the crossing device is introduced into the vascular system of the subject via the access;
  the implant housing is advanced through the vascular system to the target site, the target site being a site in the first blood vessel which is in proximity to the second blood vessel;
  a puncture is made in the first blood vessel and the second blood vessel;
  the implant of the invention is advanced such that the hands of the sutureless anastomosis device are deployed to create a first and a second flange, in a manner that sandwiches the walls of the first blood vessel and the second blood vessel between the first and second flanges and such that the lumen of the annular structure of the implant creates a channel for the flow of blood between the first and the second blood vessels;
  the implant housing is withdrawn from the target site, such that the conduit portion of the implant is deployed in the first blood vessel proximal to the sutureless anastomosis device;
  the implant housing is withdrawn from the subject at the access site.

The general method may be implemented in various ways to achieve selected results, with hardware configured appropriately for performing the selected method. The method is applied to a subject. The subject may be any animal, for example a human patient, a test animal, or a veterinary subject. The animal may be in need of treatment for a condition, in need of a fistula, or otherwise selected. In one embodiment, the subject is a human subject in need of hemodialysis treatment. In one embodiment, the subject is a human in need of treatment for end-stage renal disease.

The type of fistula to be created will depend upon the needs of the subject. In one embodiment, the subject is in need of an arteriovenous fistula. In one embodiment, the subject is in need of a venous-venous fistula, for example in a subject in need of treatment for portal venous hypertension.

The entry site will be a site selected based upon its accessibility and its proximity to the target site. For example, in one embodiment, the target site is the cephalic vein or the basilica vein in the upper arm between the shoulder and the elbow, for example as denoted 101 in FIG. 1A. An access at this introduction site may be created by any means known in the art, for example, by a needle. In one embodiment, access is created by the use of a hemostatic valve, also known as an introducer sheath. For example, the introducer sheath may comprise a needle, dilator, and sheath portion, wherein the needle is used to first pierce the blood vessel, the dilator is used to widen the opening created by the needle, and a sheath is introduced to hold the access tract open and to protect the vessel from trauma as the crossing device is introduced, used, and withdrawn. The implant housing of the crossing device is introduced through the sheath into the tract.

The advancement of the implant housing through the vasculature to the target site may be achieved as known in the art, for example, by the use of a conjoined guide wire and/or guided by visualization of the vasculature and the one or more markings of the crossing device, e.g., echogenic markings visualized by ultrasound or radiopaque marking visualized by fluoroscope, etc. The advancement of the implant housing may be achieved by the Seldinger technique, as known in the art. In one embodiment, the introduction site is the cephalic vein or the basilica vein in the upper arm and the implant housing is advanced in the efferent direction until it reaches the target site.

The location of the target site will depend upon the type of fistula to be created. In one embodiment, the fistula is an arteriovenous fistula, the first blood vessel is the median cubital perforator, connecting to either the medial cubital vein, cephalic vein or basilic vein of the arm. The second blood vessel is the brachial artery at its terminus or the proximal radial or proximal ulnar arteries. Alternative targets include any location that has a perforator branch connecting the superficial venous system to the deep venous system, including those of the upper arm basilic or forearm basilic or forearm cephalic systems. Other alternatives include perforator connections between superficial and deep systems in the lower leg, as found in the saphenous system.

In one implementation of the invention, the placement of the implant housing at the target site is achieved by the use of a complementary magnetic placement device. The placement device is introduced at an access site in the second blood vessel, for example, by way of an introducer sheath. The second access site will be a site in proximity to the skin and accessible to the target site of the second blood vessel, for example, the radial artery or ulnar artery of the lower arm below the elbow, as denoted 104 and 105 in FIG. 1A. The distal tip of the placement device is then advanced to the target site of the second blood vessel, for example, by aid of a guide wire and imaging of one or more markings on the distal tip of the placement device. When the implant housing is present at the target site of the first blood vessel and the distal tip of the placement device is present at the target site of the second blood vessel, the attractive forces of the complementary magnetic elements of the two devices will create a pinching force to hold the first and second blood vessels in alignment.

In those implementations of the invention wherein the complementary placement device comprises a hollow chamber, the complementary magnetic elements of the crossing device and the complementary placement device may be configured such that the cutting element of the crossing device and/or the guide wire of the crossing device will be received by the hollow chamber of the placement device, for example, as depicted in FIG. 2A-2I.

In an alternative embodiment, only the crossing device is utilized and the implant housing is aligned at the target site without the aid of a placement device or magnetic elements.

In one embodiment, the fistula is an AVF fistula, the first blood vessel is the median cubital perforator, and the second blood vessel is the brachial artery, for example, wherein the target site of the second blood vessel is the region of the brachial artery just the branching of the brachial artery into the ulnar and radial arteries. In alternative implementations, either the ulnar or radial artery may serve as the second blood vessel, with the target site being a position in the ulnar or radial artery below the terminal branch of the brachial artery, typically in proximity to the cubital fossa.

In most implementations of the invention, upon placement of the implant housing at the target site (optionally aided by the complementary placement device), the one or more cutting elements is deployed, creating a puncture of the first blood vessel and the second blood vessel. In one embodiment, a guide wire is extended from the implant housing in first blood vessel into the second blood vessel, followed by introduction of the distal tip of the implant housing across the punctured wall of the first blood vessel a short distance into the lumen of the second blood vessel, for example, 1-5 mm, such that the implant exit is present within the second blood vessel. Intraluminal position of the implant housing may be confirmed by the return of arterial blood through the proximal end of the crossing device, as visualized by ultrasound or fluoroscopy and/or needle tip position may be confirmed with ultrasound.

Figure 2B:
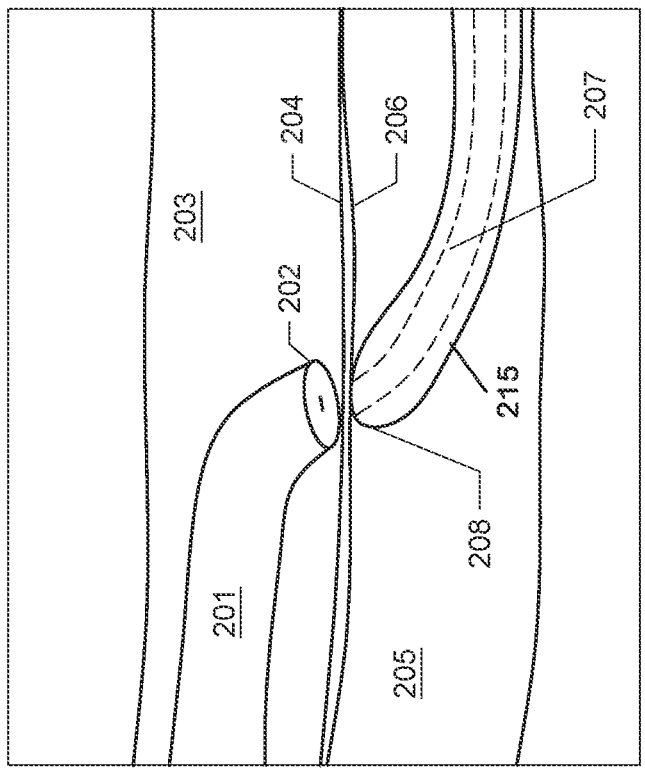
FIGS. 2A, 2B, 2C, 2D, 2E, 2F, 2G, 2H, and 2I.
Figure 2A:
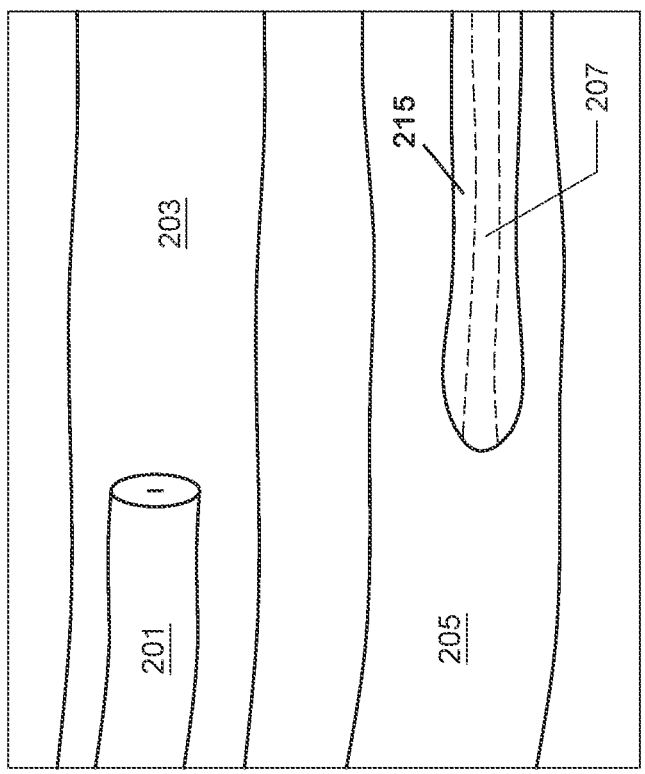
Figure 2D:
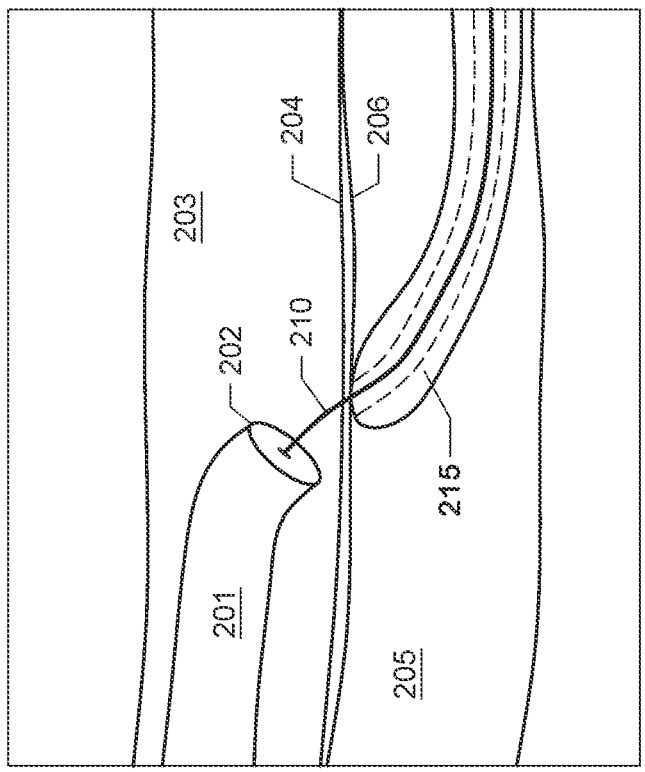
Figure 2C:
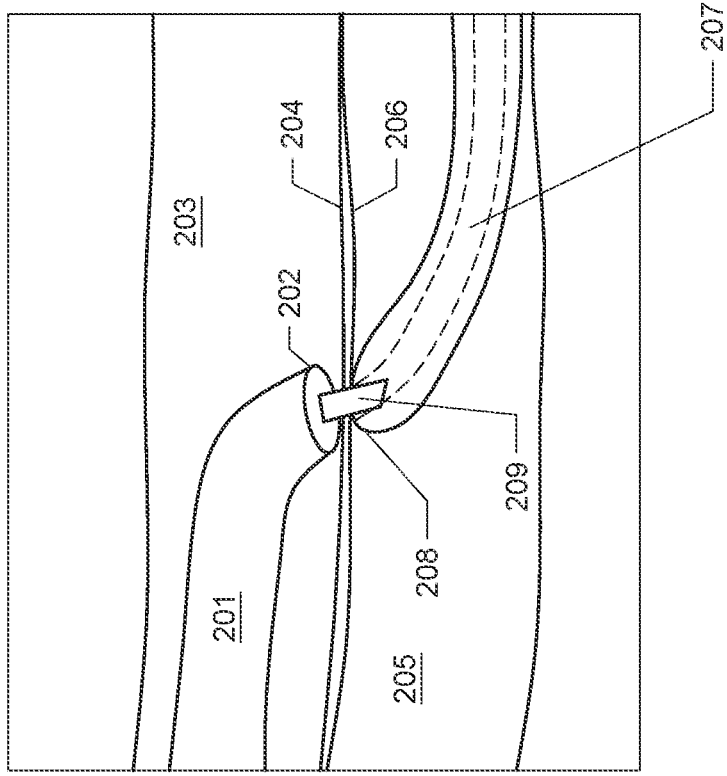
Figure 2F:
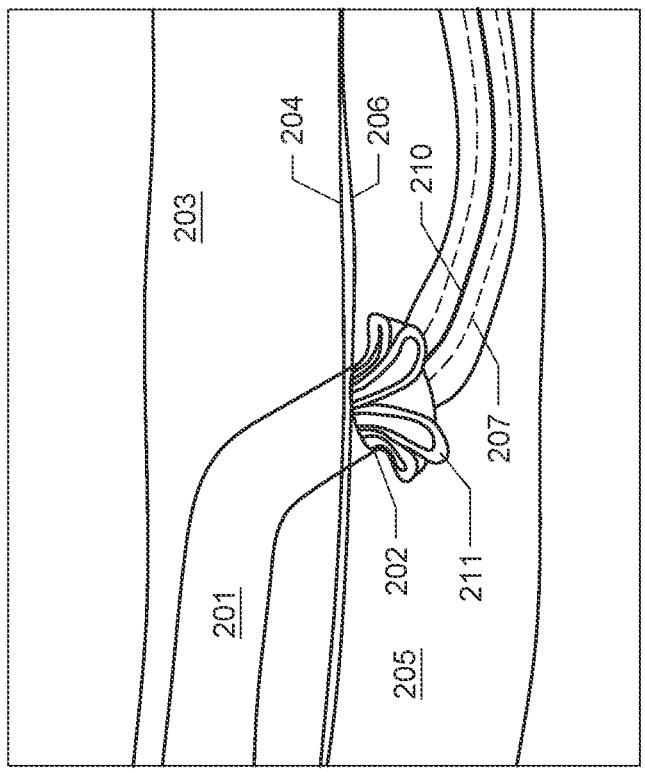
Figure 2E:
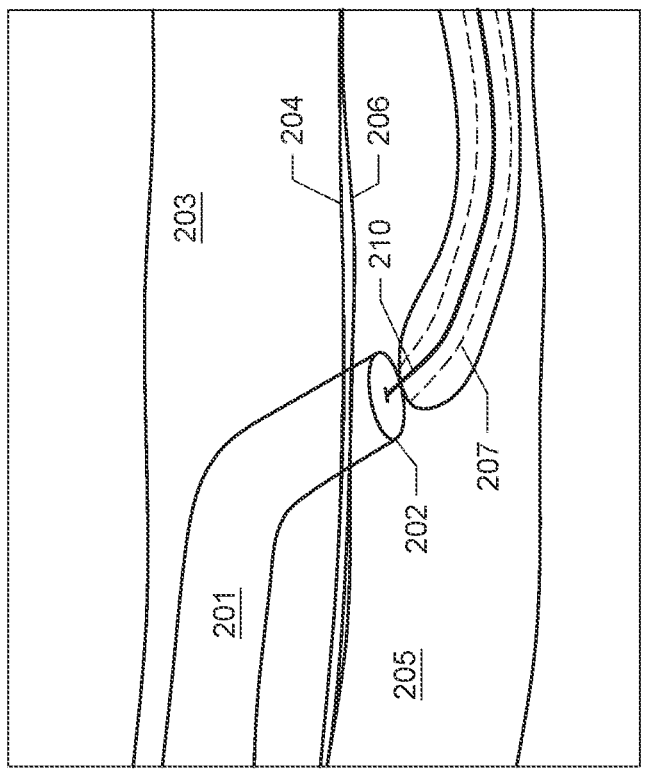
Figure 2H:
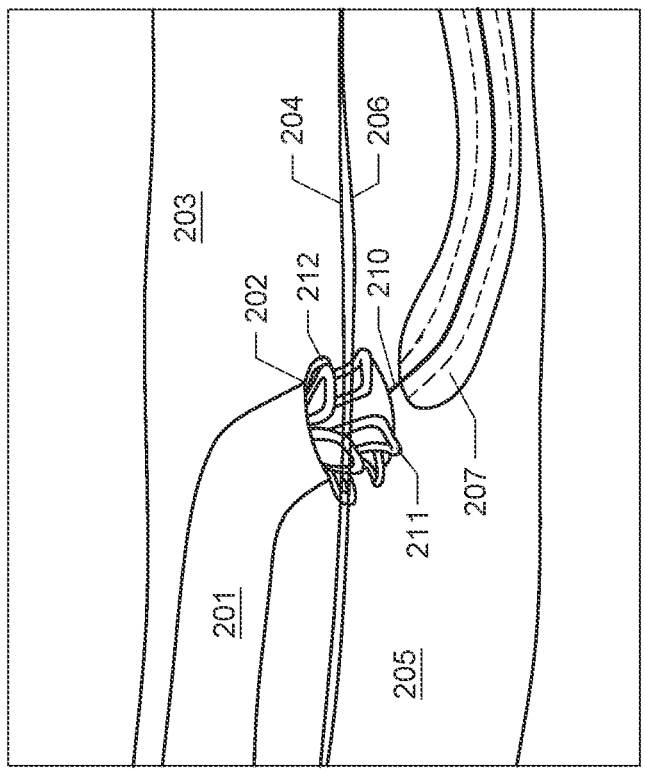
Figure 2G:
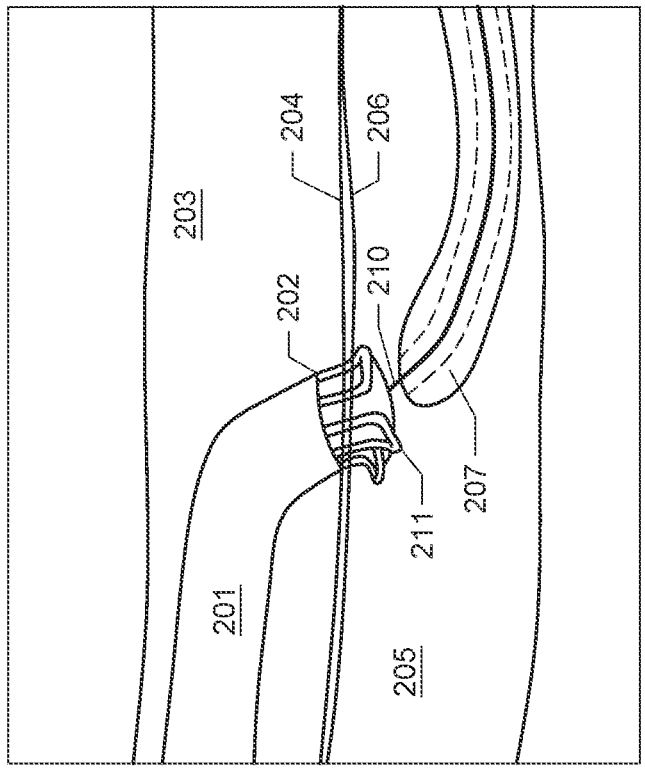
Figure 2I:
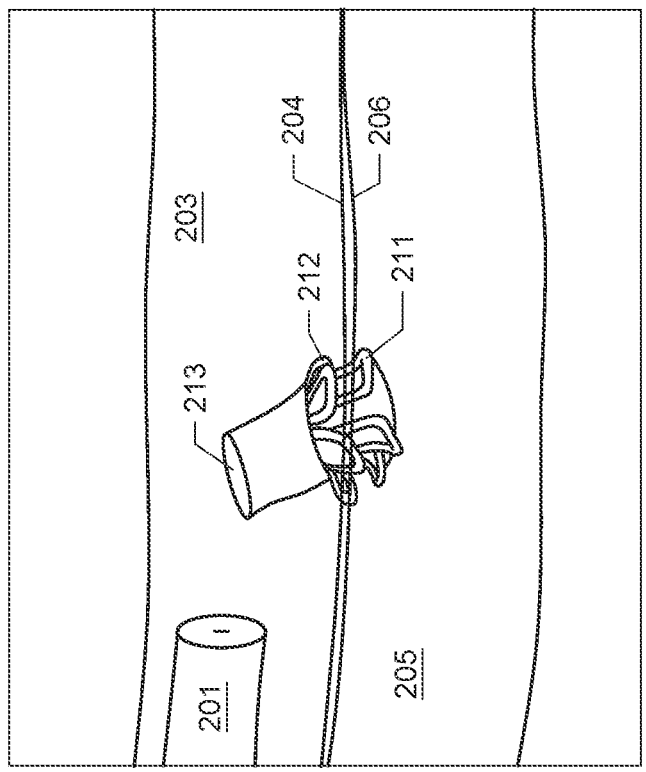
Figure 4A:
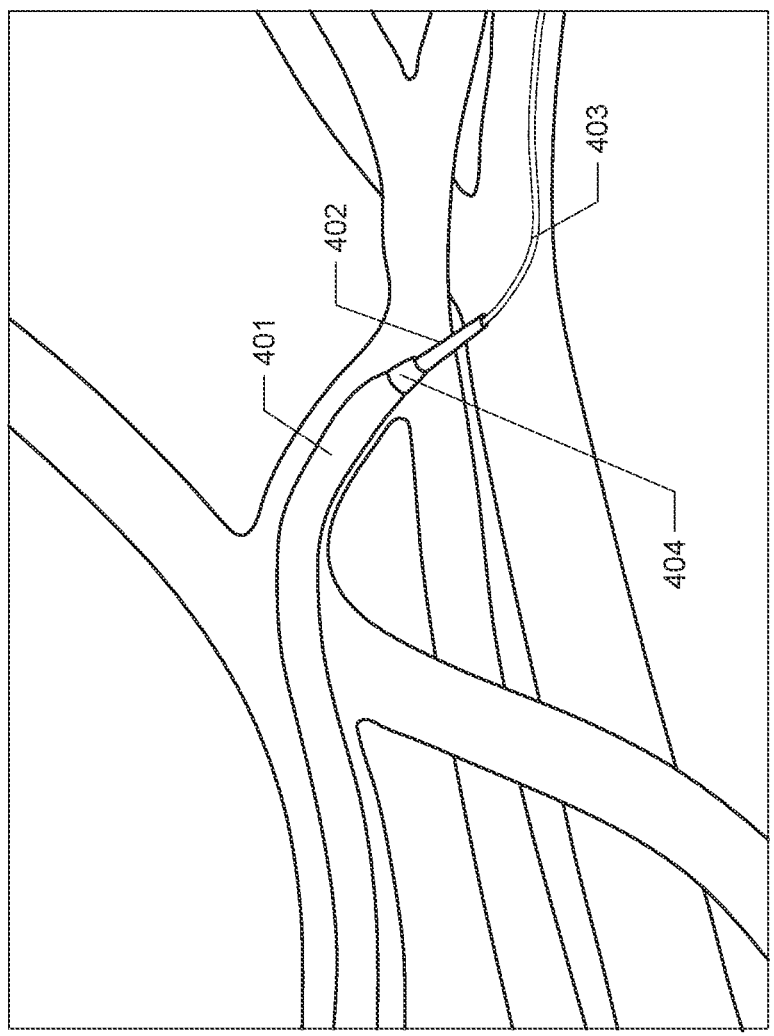
FIGS. 4A, 4B, 4C, 4D, and 4E.
Figure 4B:
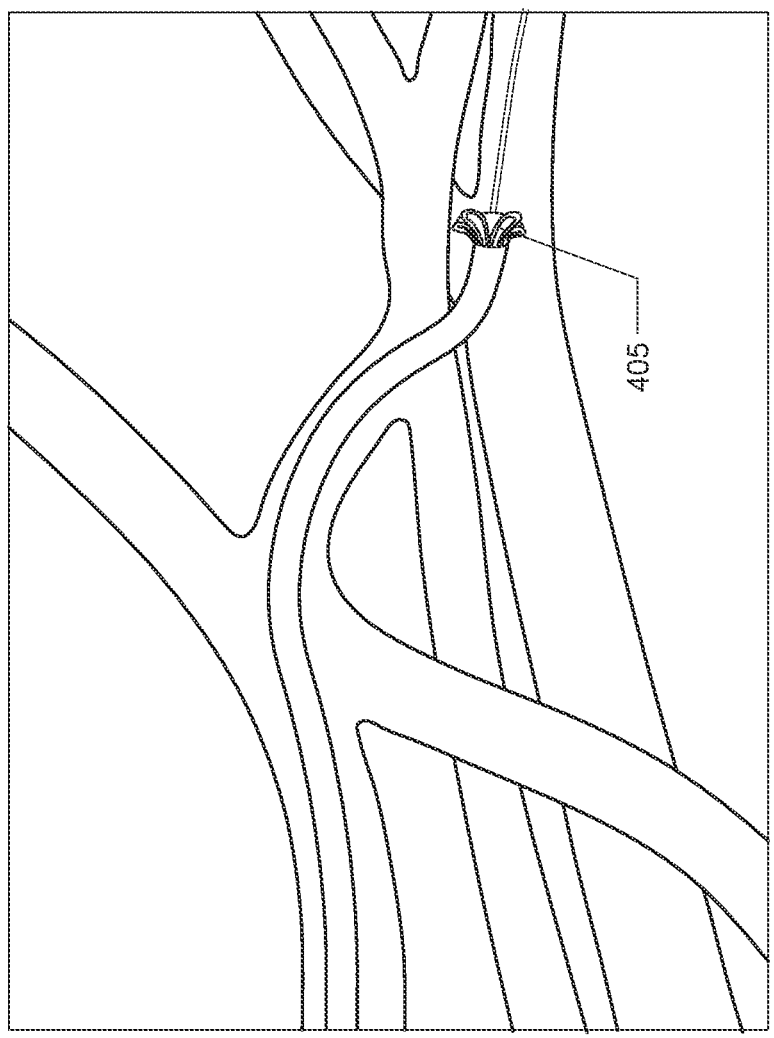
Figure 4C:
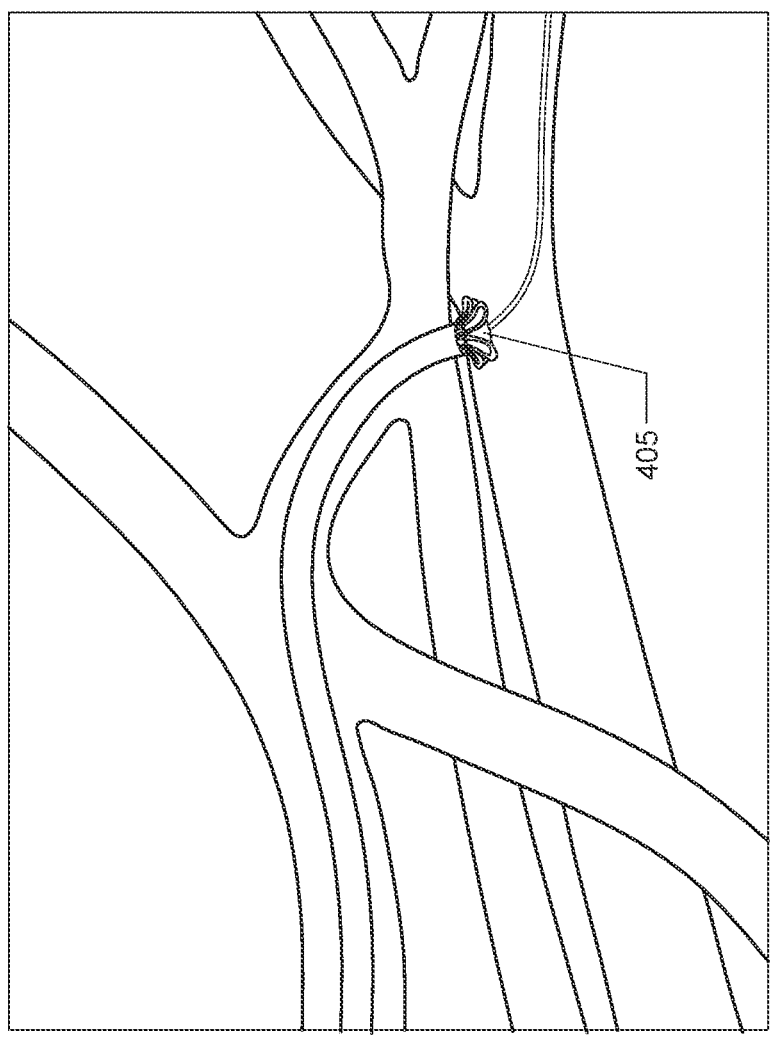
Figure 4D:
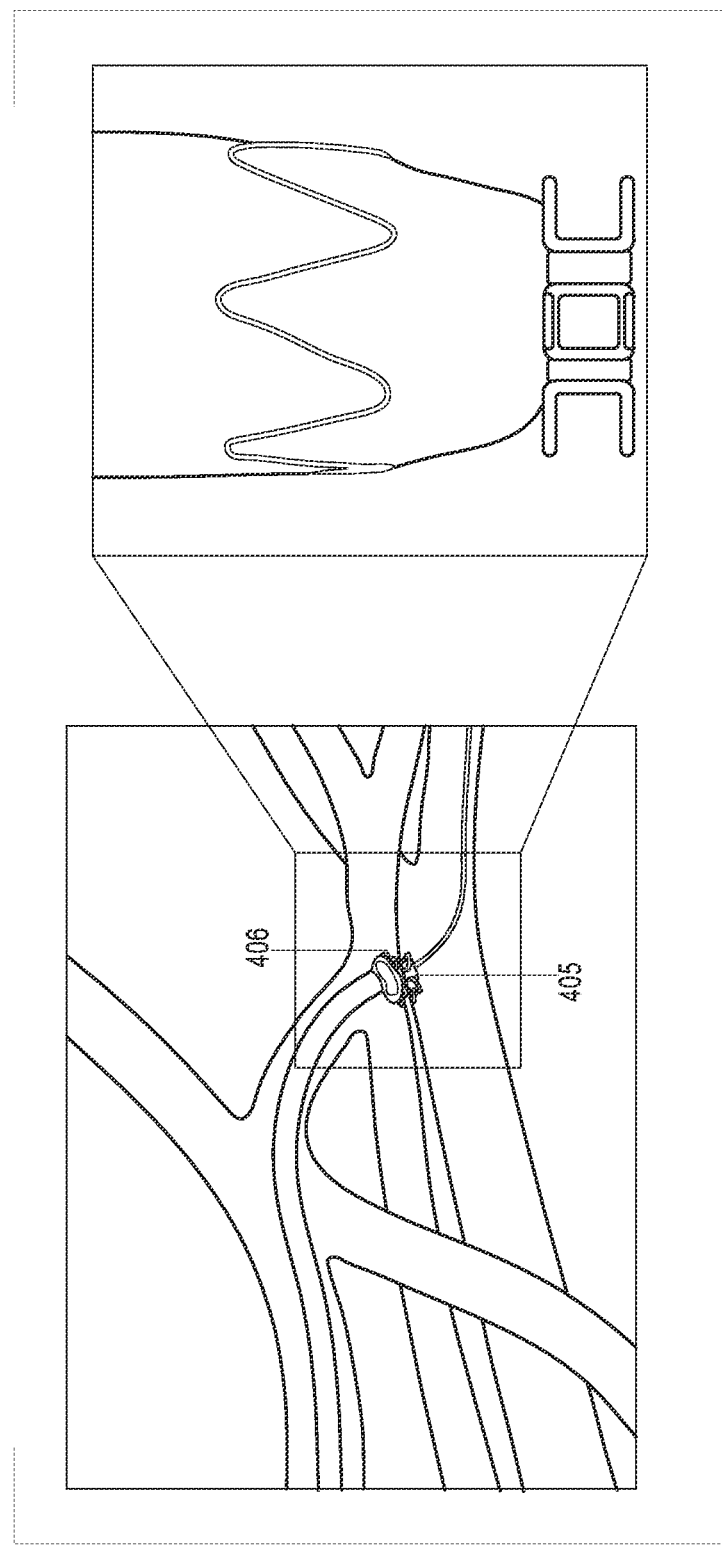
Figure 4E:
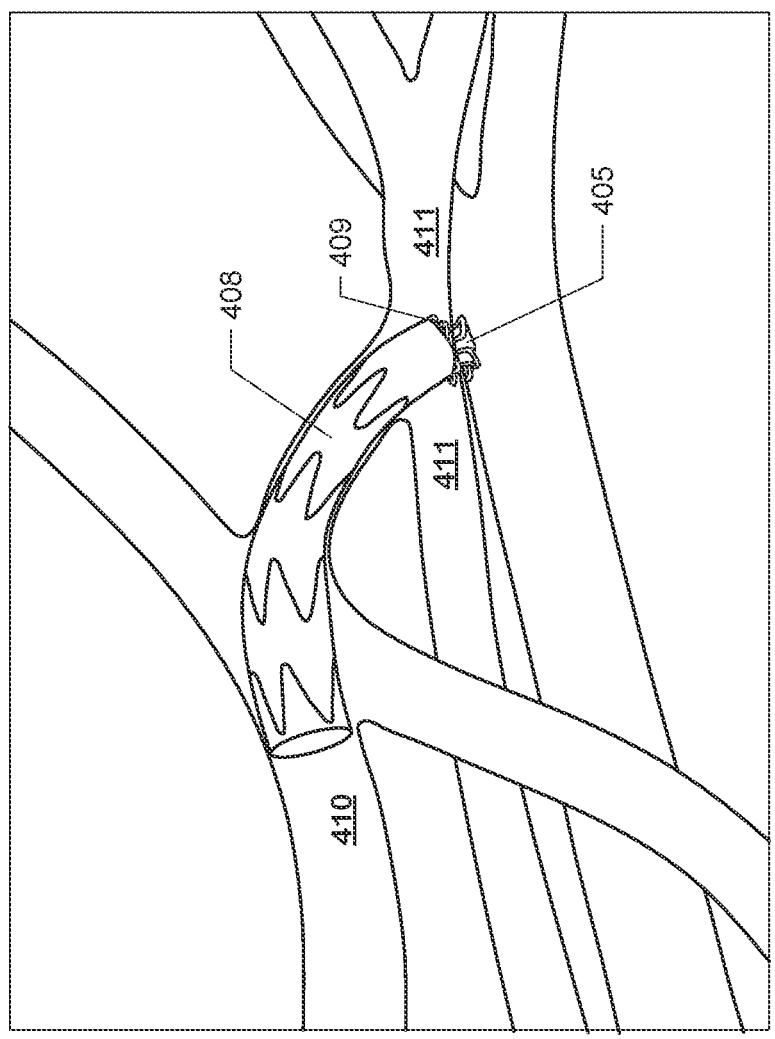

Following crossing of the distal tip of the implant housing across the puncture to the second blood vessel, the implant may be deployed. The deployment of the implant comprises the following process:

first, by means of the control elements in the control housing, an actuator in the implant housing is activated such that the distal end of the implant is advanced a first distance from the implant housing exit; wherein the first set of hands is deployed, wherein upon release of the hands from their deformed, tensioned position in the implant housing, the hands will spontaneously revert to their deployed, unconstrained position substantially perpendicular to the long axis of the implant (for example, as depicted in FIG. 2F);

second, the implant housing is slightly withdrawn such that the flange formed by the first set of deployed hands is pulled back against the second blood vessel wall, pressing it against the neighboring first blood vessel wall, and such that the implant exit of the second flange is just within the first blood vessel (for example, as depicted in FIG. 2G);

third, by means of the control elements at in the control housing, the actuator in the implant housing is activated such that the distal end of the implant is further advanced to a second distance from the implant housing exit; wherein the second set of hands is deployed, wherein the release of the second set of hands from their deformed, tensioned position in the implant housing results in their spontaneous unfolding to the unconstrained position substantially perpendicular to the long axis of the implant (for example, as depicted in FIG. 2H); and fourth, the implant housing is withdrawn from the target site such that the conduit section of the implant, held in place by the deployed flanges, fully withdraws from the implant exit (for example, as depicted in FIG. 2I), leaving the implant and a fistula formed thereby in place.

The result of the method is the formation of a fistula, such as an AVF, in a short time by a non-surgical procedure. The fistulas of the invention, being formed by a non-surgical procedure and by the novel use of a sutureless anastomosis device, may be provided with minimal trauma, greatly reducing inflammation, complications, and the frequency of follow-up intervention.

Following AVF formation, an appropriate entry site may be selected for dialysis access, sufficiently superficial to the skin to allow for repeated venipuncture (within 2 cm). For example, the brachial vein of the upper arm or radial or ulnar arteries of the lower arm below the elbow.

Modifications of the above-described process are within the scope of the invention, and, likewise, the implant and crossing devices may be implemented by various alternative configurations. For example, in an alternative embodiment, the cutting elements are present on the complementary placement device.

Exemplary Embodiments

The foregoing description will enable one of skill in the art to implement fistulas at various sites in the body, using devices and methods that embody the several inventive concepts described herein. Following is a roll of exemplary implementations of the devices and methods.

The scope of the invention encompasses an implant for the creation of a fistula between a first and a second blood vessel, the implant having a longitudinal axis from distal to a proximal end, the device comprising:
  a sutureless anastomosis device comprising a first, of hands and a second set of hands;
  wherein each hand comprises a body extending at an angle from the longitudinal axis of the implant;
  wherein each hand comprises a resilient material such that the hand may be deflected under tension to a compact orientation substantially parallel to the longitudinal axis of the implant;
  wherein each of the first set of hands and the second set of hands is connected to and arranged around an annular structure such that the first set of hands forms a first flange and the second set of hand forms a second flange, wherein the flanges are separated by a space along the longitudinal axis of the implant;
  wherein the device further comprises a conduit comprising a tubular structure comprising a lumen, connected at its distal end circumferentially around the proximal end of the annular structure, wherein the conduit comprises a scaffolding material enclosed in or surrounded by a covering of biocompatible material.

In one embodiment, the sutureless anastomosis device comprises 4-12 hands. In one embodiment, the hands are substantially perpendicular to the longitudinal axis of the device. In one embodiment, the hands comprise a material selected from the group consisting of nitinol, stainless steel, and cobalt-chrome. In one embodiment, the hands comprise loops of wire. In one embodiment, the annular structure comprises an expandable structure. In one embodiment, the conduit is tapered, being widest at its proximal end and narrowest at its distal end where it connects to the annular structure. In one embodiment, the covering of the conduit comprises PTFE film.

In one implementation, the invention encompasses a method of creating an AVF by the implant device above. In a related implementation, the scope of the invention encompasses the implant described above, for use in the creation of a fistula between a first and a second blood vessel, wherein blood will flow from the second vessel through the annular structure of the sutureless anastomosis device and into the first vessel via the lumen of the conduit. In one embodiment, the fistula is an arteriovenous fistula. In one embodiment, the first blood vessel is the median cubital perforator, connecting to either the medial cubital vein, cephalic vein or basilic vein of the arm and the second blood vessel is the brachial artery at its terminus or the proximal radial or proximal ulnar artery. In one embodiment, the arteriovenous fistula is created in a subject in need of dialysis treatment. In one embodiment, the conduit of the implant is deployed such that blood flowing from the second blood vessel through the conduit bypasses the deep venous system and flows into the superficial venous system.

In one implementation, the scope of the invention encompasses a crossing device for deploying the implant described above, comprising
  a catheter comprising proximal end comprising a control assembly and a distal end comprising an implant housing;
  wherein the implant housing comprises a deployable cutting element, a deployable guide wire; a space for storing the fistula device of any of claims 1-9 such that the hands are in the compact position; an opening for the implant to exit the implant housing; and a means of controllably and incrementally advancing the implant from the opening;
  wherein the deployable cutting element, the deployable guide wire; and the means for controllably and incrementally advancing the implant from the opening are controlled by means of control elements in the control housing.

In one embodiment, the implant housing comprises one or more echogenic and/or radiopaque markings for visualization of the device when deployed in the body of a subject. In one embodiment, the implant housing comprises one or more magnetic elements.

The scope of the invention further encompasses a method of forming a fistula in a subject wherein the fistula comprises a connection between a first and a second blood vessel in a subject, comprising the steps:
  creating an access at a selected entry site of the subject;
  introducing a crossing device into the vascular system of the subject via the access, wherein the crossing device comprises an implant housing which houses an implant, wherein the implant may be controllably deployed from the implant housing; wherein the implant comprises a sutureless anastomosis device comprising an annular structure comprising a first set of hands and a second set of hands wherein the each of the first set of hands and second set of hands are circumferentially arranged around the outer diameter of the annular structure; wherein the each set of hands may be separately released from the implant housing; wherein upon release from the implant housing, each set of hands spontaneously assumes a configuration which creates a flange; wherein the implant further comprises a conduit portion extending from the proximal end of the annular structure; wherein the implant housing further comprises a deployable cutting element;
  advancing the implant housing of the crossing device through the vascular system to the target site, the target site being a site in the first blood vessel which is in proximity to the second blood vessel;
  deploying the cutting element to create a puncture in the first blood vessel and the second blood vessel;
  advancing the implant from the implant housing to create the first and the second flange in a manner that sandwiches the walls of the first blood vessel and the second blood vessel between the first and second flanges and such that the lumen of the annular structure of the implant creates a channel for the flow of blood between the first and the second blood vessels;
  withdrawing the implant housing from the target site, such that the conduit portion of the implant is deployed in the first blood vessel.

In one embodiment, the subject is a human subject. In one embodiment, the subject is a human subject in need of hemodialysis. In one embodiment, the fistula is an arteriovenous fistula. In one embodiment, the fistula is a venous-venous fistula. In one embodiment, the first blood vessel is the brachial vein, the access site is the cephalic vein or the basilica vein in the upper arm, and the target site is the brachial vein wherein it is in proximity to the brachial artery, ulnar artery, or radial artery. In one embodiment, the second blood vessel is the brachial artery, the ulnar artery, or the radial artery. In one embodiment, the target site is in the proximity to the branching of the brachial artery into the ulnar and radial arteries. In one embodiment, the implant housing comprises one or more magnetic elements and the method further encompasses the use of a placement device comprising one or more magnetic elements at its distal tip, which distal tip is advanced to the target site in the second blood vessel, such that the proximity of magnetic elements of the implant housing and placement device causes the two structures to pinch the first and second blood vessel walls together.

In one embodiment, the implant of the invention is deployed from the crossing device by the following process:

first, by means of the control elements at the proximal control housing, an actuator in the implant housing is activated such that the distal end of the implant is advanced a first distance from the implant housing exit; wherein the first set of hands is deployed, such that the distal hands of the implant's sutureless anastomosis device are liberated from their deformed, tensioned position in the implant housing and can spontaneously revert to their deployed, unconstrained position substantially perpendicular to the long axis of the implant;

second, the implant housing is slightly withdrawn such that the flange formed by the first set of deployed hands is pulled back against the second blood vessel wall, pressing it against the neighboring first blood vessel wall, and such that the implant exit of the second flange is just within the first blood vessel;

third, by means of the control elements at the proximal control housing, the actuator in the implant housing is activated such that the distal end of the implant is further advanced to a second distance from the implant housing exit; wherein the second set of hands is deployed, such that the proximal hands of the implant's sutureless anastomosis device are liberated from their deformed, tensioned position in the implant housing and can spontaneously revert to a deployed, unconstrained position substantially perpendicular to the long axis of the implant; and fourth, the implant housing is withdrawn from the target site such that the conduit section of the implant, held in place by the deployed flanges, fully withdraws from the implant exit, leaving the implant in place and a fistula formed thereby.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of bringing into contact a wall of a first blood vessel and a wall of a second blood vessel in a subject, the method comprising: advancing a first catheter having a magnetized end face through the first vessel to a target site; advancing a second catheter having a magnetized end face through the second vessel to the target site, wherein magnetic attraction between the magnetized end faces of the first and second catheters brings a wall of the first blood vessel into contact with a wall of the second blood vessel at the target site, wherein the first blood vessel is a deep artery and the second blood vessel is a superficial vein.

2. The method of claim 1, further comprising piercing the walls of the first and second blood vessels in contact with each other.

3. The method of claim 2, wherein the piercing is performed using a cutting element deployed from the end face of the first catheter.

4. The method of claim 3, further comprising retracting the deployed cutting element into the first catheter subsequent to piercing the walls of the first and second blood vessels.

5. The method of claim 3, wherein the cutting element is a guide wire comprising a needle tip deployed to act as both the cutting element and a guide wire.

6. The method of claim 2, further comprising extending a guide wire from the end face of the first catheter into a lumen of the second catheter via the end face of the second catheter.

7. The method of claim 6, further comprising extending the end face of the first catheter into the second blood vessel.

8. The method of claim 7, wherein the first catheter houses an anastomosis device, and wherein the method further comprises deploying the anastomosis device to create a fistula between the first and second blood vessels at the target site.

9. The method of claim 8, wherein the anastomosis device comprises: an annular body comprising an opening; a first set of deployable hands, and a second set of deployable hands.

10. The method of claim 9, wherein deploying the anastomosis device comprises partially ejecting the anastomosis device from the magnetic end face of the first catheter such that the first set of hands of the anastomosis device is deployed inside the second vessel.

11. The method of claim 10, wherein deploying the anastomosis device further comprises withdrawing the first catheter into the first blood vessel such that the tip of the first catheter is pulled back into the first blood vessel and the first set of hands catch the wall of the second blood vessel.

12. The method of claim 11, wherein deploying the anastomosis device further comprises ejecting the anastomosis device from the first magnetic end face of the first catheter to deploy the second set of hands of the anastomosis device such that the walls of the first and second blood vessels are sandwiched between the first set of hands and the second set of hands of the anastomosis device.

13. The method of claim 1, wherein the magnetized end face of the first catheter and the magnetized end face of the second catheter comprise ring shaped magnets that define the end faces of the first catheter and the second catheter.

14. The method of claim 13, wherein the center portion of the magnetized end face of the first catheter and the magnetized end face of the second catheter is hollow and allows advancement of a cutting element and a guide wire.

15. The method of claim 1, further comprising creating a fistula between the first and second blood vessels at the target site.

* * * * *